(12) United States Patent
Yeung et al.

(10) Patent No.: US 7,803,234 B2
(45) Date of Patent: Sep. 28, 2010

(54) SURFACE TREATED SHAPE MEMORY MATERIALS AND METHODS FOR MAKING SAME

(75) Inventors: Kelvin W. K. Yeung, Tai Wai (HK); Ray W. Y. Poon, Kowloon (HK); Paul Kim-Ho Chu, Kowloon (HK); Kenneth M. C. Cheung, Mid-Levels (HK); William W. Lu, Hong Kong (HK)

(73) Assignees: Versitech Limited, Hong Kong (CN); The City University of Hong Kong

( * ) Notice: Subject to any disclaimer, the term of this patent is extended or adjusted under 35 U.S.C. 154(b) by 418 days.

(21) Appl. No.: 11/331,264

(22) Filed: Jan. 11, 2006

(65) Prior Publication Data

US 2006/0157159 A1    Jul. 20, 2006

Related U.S. Application Data

(60) Provisional application No. 60/643,744, filed on Jan. 13, 2005.

(51) Int. Cl.
    C23C 8/36    (2006.01)
(52) U.S. Cl. ........................................ 148/239; 427/539
(58) Field of Classification Search ................ 428/450, 428/520; 148/239; 427/539
    See application file for complete search history.

(56) References Cited

U.S. PATENT DOCUMENTS

2002/0009604 A1 *   1/2002   Zamora et al. .............. 428/450

OTHER PUBLICATIONS

Berger-Gorbet, M. et al., "Biocompatibility Testing of NiTi Screws Using Immunohistochemistry . . . ," J. Biomed. Mater. Res., 1996, 243-248, vol. 32.
Jia, W. et al., "Nickel Release from Orthodontic Arch Wires and Cellular Immune Response to . . . ," J. Biomed. Mater. Res., 1999, 488-495, vol. 48.
Es-Souni, M. et al., "On the Properties of Two Binary NiTi Shape Memory Alloys. Effects on Surface Finish . . . ," Biomaterials, 2002, 2887-2894, vol. 23.
Shih, C-C. et al., "The Cytotoxicity of Corrosion Products of Nitinol Stent Wire on Cultured Smooth Muscle Cells," J. Biomed. Mater. Res., 2000, 395-403, vol. 52.
Kapanen, A. et al., "Behaviour of Nitinol in Osteoblast-like ROS-17 Cell Cultures," Biomaterials, 2002, 645-650, vol. 23.
Kapanen, A. et al., "TGF-$\beta$1 Secretion of ROS-17/2.8 Cultures on NiTi Implant Material," Biomaterials, 2002, 3341-3346, vol. 23.
Blanco-Dalmau, L. et al., "A Study of Nickel Allergy," Journal of Prosthetic Dentistry—Research and Education, 1984, 116-119, vol. 52, No. 1.

(Continued)

Primary Examiner—George Wyszomierski
Assistant Examiner—Weiping Zhu
(74) Attorney, Agent, or Firm—Saliwanchik, Lloyd & Saliwanchik

(57) ABSTRACT

The invention provides a method for making surface treated shape memory materials such as from NiTi alloy using plasma immersion ion implantation and deposition and related ion-beam and plasma-based techniques to alter the surface properties of those materials primarily for biomedical applications. The surfaces are treated with nitrogen, oxygen, and carbon, but become bio-inactive after implanted with other elements such as silicon.

25 Claims, 2 Drawing Sheets

OTHER PUBLICATIONS

Lamster, I. B. et al., "Rapid Loss of Alveolar Bone Associated with Nonprecious Alloy Crowns in Two Patients . . . ," Nickel Hypersensitivity, 1986, 486-492, vol. 58, No. 7.

Espana, A. et al., "Chronic Urticaria After Implantation of 2 Nickel-Containing Dental Prostheses in a Nickel-Allergic Patient," Contact Dermititis, 1989, 204-205, vol. 21.

Sanford, W. E., and Nieboer, E. "Renal Toxicity of Nickel in Humans," Nickel and Human Health: Current Perspectives, 1992, 123-134.

Wu, S. K. and Lee, C. Y., "A Study of Vacuum Carburization of An Equiatomic TiNi Shape Memory Alloy," Scripta Materialia, 1997, 837-842, vol. 37, No. 6.

Huber, P. et al., "Formation of TiN, TiC and TiCN by Metal Plasma Immersion Ion Implantation and Deposition," Surface and Coatings Technology, 2003, 1243-1247.

Liu, N. et al., "Effect of Nano-Micro TiN Addition on the Microstructure and Mechanical Properties of TiC Based Cermets," J. Europ. Ceramic Society, 2002, 2409-2414, vol. 22.

Oliveira, M.M. and Bolton, J.D., "High-Speed Steels: Increasing Wear Resistance by Adding Ceramic Particles," Journal of Materials Processing Technology, 1999, 15-20.

Vaz, F. et al., "Structural, Optical and Mechanical Properties of Coloured TiNxOy Thin Films," Thin Solid Films, 2004, 449-454, vol. 447-448.

Kola, P. V. et al., "Magnetron Sputtering of Tin Protective Coatings for Medical Applications," Journal of Materials Processing Technology, 1996, 422-430, vol. 56.

Tan, L. and Crone, W.C., "Surface Characterization of NiTi Modified by Plasma Source Ion Implantation," Acta Materialia, 2002, 4449-4460, vol. 50.

Mandl, S. et al., "Investigation on Plasma Immersion Ion Plantation Treated Medical Implants," Biomolecular Engineering, 2002, 129-132, vol. 19.

Nie, X. et al., "Deposition of Layered Bioceramic Hydroxyapatite/TiO2 Coatings on Titanium Alloys Using . . . ," Surface and Coatings Technology, 2000, 407-414, vol. 125.

Lackner, J.M. et al., "Pulsed Laser Deposition of Titanium Oxide Coatings at Room Temperature . . . ," Surface and Coatings Technology, 2004, 585-590, 180-181.

Li, M. et al., "Corrosion Behavior of TiN Coated Type 316 Stainless Steel in Simulated PEMFC Environments," Corrosion Science, 2004, 1369-1380, vol. 46.

Wan, G.J. et al., "TiN and Ti-O/TiN Films Fabricated by PIII-D for Enhancement of Corrosion . . . ," Surface & Coatings Technology, 2004, 136-140, vol. 186.

Pfhol, C. et al., "Evaluation of the Corrosion Behaviour of Wear-Resistant PACVD Coatings," Surface & Coatings Technology, 1999, 114-117, vol. 112.

Maiya, P.S. et al., "Failure and Corrosion Resistance of TiN and TiC Coatings Deposited on Graphite . . . ," Surface & Coatings Technology, 1998, 218-222, vol. 102.

Leng, Y.X. et al., "Structure and Properties of Biomedical TiO2 Films Synthesized by Dual Plasma Deposition," Surface & Coatings Technology, 2002, 295-300, vol. 156.

\* cited by examiner

SURFACE TREATED SHAPE MEMORY MATERIALS AND METHODS FOR MAKING SAME

This application claims priority of provisional application U.S. Ser. No. 60/643,744, filed Jan. 13, 2005, the contents of which are incorporated herein by reference.

BACKGROUND OF THE INVENTION

Shape memory materials such as nickel titanium (NiTi) alloys are promising materials for surgical implants in orthopedics due to their unique shape memory effect (SME) and super-elasticity (SE) that other common orthopedic materials such as stainless steels and titanium alloys do not possess. Their mechanical properties are also closer to that of cortical bones than stainless steels and titanium alloys. The materials display superior wear resistance to CoCrMo alloys used in bone trauma fixation. Several other favorable properties of the materials have also been investigated, and good bio-compatibility has also been reported. However, some negative effects have also been pointed out. For example, Berger-Gorbet et al. have found that the osteogenesis process and osteonectin synthesis activity in NiTi alloys are unfavorable compared to stainless steels and titanium alloys.[1] Jia et al. in their study revealed that the cell death rate was severe on NiTi alloys.[2]

These problems are believed to stem from the poor corrosion resistance of the materials, which may lead to an increase in their cytotoxicity. It is most likely that some toxic components released from the substrate cause the cell death rather than the apoptosis.[3] Shih et al. reported that the supernatant and corrosive products from NiTi may result in the death of smooth muscle cells, especially when the amount of released nickel is higher than 9 ppm.[4] A few other studies have also reported that nickel ions[5,6] leached from the alloys cause allergic reactions in nickel hyper-sensitive patients.[7-10] While the homogeneity of the materials microstructures and the surface morphology may alter the anti-corrosion ability of NiTi alloys, there is no doubt that the corrosion resistance and anti-wear properties of the materials must be enhanced before the materials can be widely used clinically, especially as orthopedic implants with couplings where fretting is expected.

Titanium carbides and nitrides have excellent mechanical and chemical properties, for example, good wear resistance, inactive with numbers of chemical substances and outstanding hardness [11-16]. Titanium oxides are known to be fairy compatible with living tissues [17-20]. They are also inactive to many chemical reactions. In surface coating industries, these elements have been applied to improve the mechanical and corrosion properties of the substrates through various methods [21-25] for a period of time.

SUMMARY OF THE INVENTION

The invention provides a method for the altering surface composition of a nickel titanium alloy part to increase biocompatibility, comprising implanting nitrogen, oxygen or carbon on the surface of the nickel titanium alloy part by plasma immersion ion implantation, or deposition, or ion beam immersion or implantation. The surface may also be altered by plasma immersion ion implantation and deposition or related ion-beam and plasma-based techniques such as plasma-enhanced vapor phase deposition (PECVD), physical vapor deposition (VPD), and chemical vapor deposition (CVD).

The invention also provides orthopedic, vascular, and esophageal implants made from the foregoing materials.

DETAILED DESCRIPTION OF THE PREFERRED EMBODIMENTS OF THE INVENTION

Figure 1:
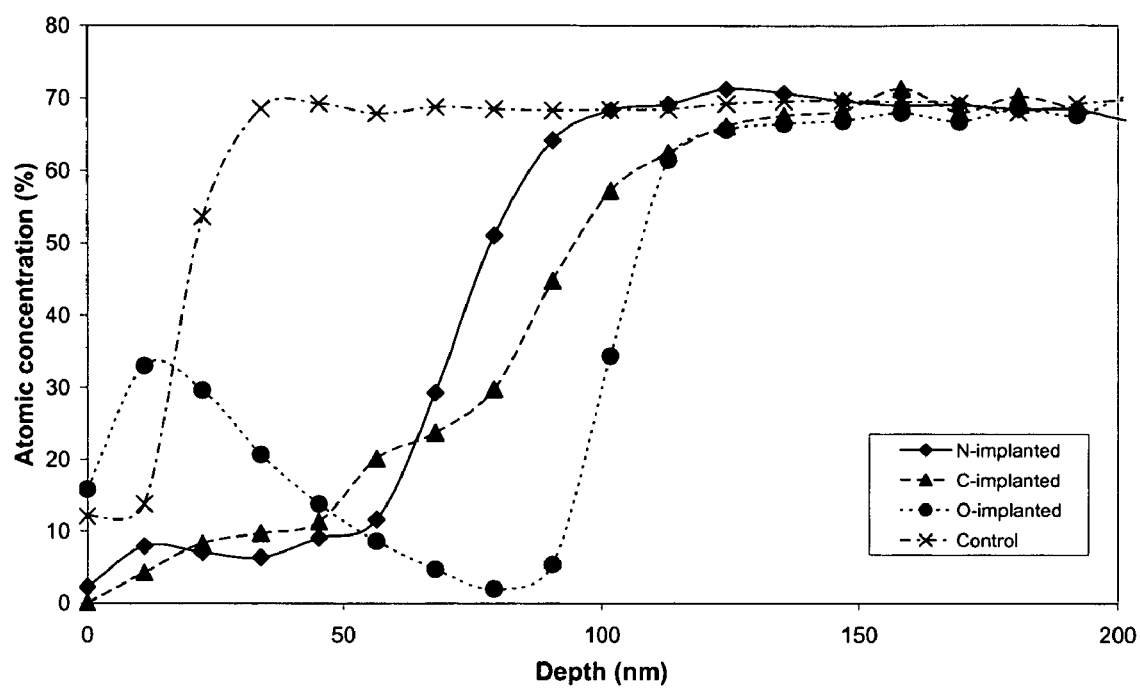
FIG. 1 is a plot of Ni depth profiles acquired from the nitrogen, acetylene and oxygen PIII surface treated samples and control.

Shape memory materials such as nickel titanium alloys (NiTi) are useful materials in biomedical applications due to their unique properties. However, for prolonged use in a human body, deterioration of the corrosion resistance of the materials becomes a critical issue, because of the possibility of deleterious ions released from the substrate to living tissues. Therefore, we suggested the use of plasma immersion ion implantation and deposition and related ion-beam and plasma-based techniques to implant some other elements, such as $C_2H_2$, $N_2$, and $O_2$, into NiTi substrates to alter corrosion resistance and wear properties of the alloys. We have successfully demonstrated that the corrosion resistance and wear properties of nickel titanium shape memory alloys can be enhanced by implanting nitrogen, carbon and oxygen onto the substrate surface. Additionally, with the use of plasma immersion ion implantation or deposition, the biological properties such as osteoconductivity and hydrophilicity can also be reduced or enhanced.

According to one preferred embodiment, the invention provides a method for the altering surface composition of a nickel titanium alloy part to increase biocompatibility, comprising implanting nitrogen, oxygen or carbon on the surface of the nickel titanium alloy part by plasma immersion ion implantation, or deposition, or ion beam immersion or implantation. The nickel titanium alloy is preferably a shape memory alloy, and has a nickel content ranging from about 20-80% of nickel and 80-20% of titanium. The surface implantation of elements enhances the mechanical properties of the alloy, such as hydrophilicity, corrosion and wear resistance. The nickel titanium alloy part can be reduced or enhanced. In practicing the invention, the plasma immersion ion implantation and deposition or related ion-beam and plasma-based techniques such as plasma-enhanced vapor phase deposition (PECVD), physical vapor deposition (VPD), and chemical vapor deposition (CVD) can reduce, terminate or prevent the deleterious ions from being released from the substrate of the shape memory materials. The materials may be biomaterials used for orthopedics, urologics, vascular surgery, hepatobiliary surgery or esophageal surgery. The energy of the incident species used for surface treatment of the materials ranges from 1 eV to 1 keV for deposition, 500 eV to 100 keV for implantation and deposition, and 500 eV to 10 MeV for beam-line ion implantation. Preferably, the energy of the surface treatment of the materials ranges from 1 eV to 500 eVs for deposition, 500 eVs to 1000 eVs for implantation and deposition, and 1000 to 1000 MeVs for beamline ion implantation. The direct current is applied with the parameters 0 Hz repetition with 'infinite' pulse duration to 5000 Hz. The material implanted is a nitrogen source, a carbon source, or an oxygen source, gaseous, liquid, or solid form. The nitrogen source is nitrogen gas. The carbon source is acetylene or a derivative thereof. The oxygen source is oxygen gas.

The method may be used to make an orthopedic, vascular, or esophageal implant.

For the purposes of promoting an understanding of the principles of the plasma immersion ion implantation and deposition or related ion-beam and plasma-based techniques such as plasma-enhanced vapor phase deposition (PECVD), physical vapor deposition (VPD), and chemical vapor deposition (CVD) on the surface of shape memory materials such as Ti—50.8% at Ni alloy, the specific preferred embodiments of the invention will be described.

FIG. 1 indicates the Ni concentration profiles of the samples with and without PIII surface treatment. The Ni concentrations in the implanted region in nitrogen, acetylene and oxygen plasma-implanted samples are much lower when compared to the non-coated control sample. Nitrogen PIII gives rise to the highest Ni suppression compared to oxygen PIII.

The treatment methods for acetylene, nitrogen and oxygen implantation the sample were ground, polished to a shiny surface texture, and then ultrasonically cleaned with acetone and ethanol before deposition or implantation was conducted in the plasma immersion ion implanter. The deposition and implantation parameters of acetylene, nitrogen and oxygen implantation samples were displayed in Table 1. The elemental depth profiles as shown in FIG. 1 were determined by X-ray photoelectron spectroscopy (XPS) (Physical Electronics PHI 5802, Minnesota, USA).

TABLE 1

Treatment parameters of plasma immersion ion implantation and deposition

| Sample | NiTi with acetylene implantation | NiTi with nitrogen implantation | NiTi with oxygen implantation |
|---|---|---|---|
| Gas type | $C_2H_2$ | $N_2$ | $O_2$ |
| RF | — | 1000 W | 1000 W |
| High voltage | −40 kV | −40 kV | −40 kV |
| Pulse width | 30 μs | 50 μs | 50 μs |
| Frequency | 200 Hz | 200 Hz | 200 Hz |
| Duration of implantation (min) | 90 | 240 | 240 |
| Base pressure | $1 \times 10^{-5}$ Torr | $7.0 \times 10^{-6}$ Torr | $7.0 \times 10^{-6}$ Torr |
| Working pressure | $2.0 \times 10^{-3}$ Torr | $6.4 \times 10^{-4}$ Torr | $6.4 \times 10^{-4}$ Torr |
| Dose | $5.5 \times 10^{16}$ cm$^{-2}$ | $9.6 \times 10^{16}$ cm$^{-2}$ | $1.0 \times 10^{17}$ cm$^{-2}$ |
| Annealing pressure | $1.0 \times 10^{-5}$ Torr | $8.0 \times 10^{-6}$ Torr | $8.0 \times 10^{-6}$ Torr |
| Annealing temperature (° C.) | 600 | 450 | 450 |
| Duration of annealing (h) | 5 | 5 | 5 |

Nano-indentation tests (MTS Nano Indenter XP, USA) were conducted on five areas to determine the average hardness and Young's modulus of the treated and control samples. The hardness of the control sample is 4.5 GPa and the Young's modulus is 57 GPa.

Table 2 lists the results of the hardness (H) and Young's modulus (E) of the untreated control and treated samples surfaces using nano-indentation test.

TABLE 2

Young's modulus and hardness of control and the treated samples surfaces

| Sample | NiTi | NiTi implanted with acetylene | NiTi implanted with nitrogen | NiTi implanted with oxygen |
|---|---|---|---|---|
| Young's modulus (GPa) | 57 | 110-70 | 150-65 | 115-605 |
| Hardness (GPa) | 4.5 | 9.5-4.5 | 11-5 | 8-4 |

All the surface-treated samples possess higher surface hardness and Young's modulus than those of the control. It implies that the treated surfaces are mechanically stronger than the NiTi substrates underneath and can withstand mechanical shock more effectively. Among the treated surfaces, the nitrogen-implanted layer has the largest H and E, followed by the acetylene- and oxygen-implanted layers.

Table 3 lists the amounts of Ni leached from the surface-treated and untreated samples after the electrochemical tests as determined by inductively coupled plasma mass spectrometry (ICPMS). Electrochemical tests based on ASTM G5-94 (1999) and G61-86 (1998) were performed by a potentiostat (VersaStat II EG&G, USA) using a standard simulated body fluid (SBF) at a pH of 7.42 and temperature of 3770.5 1C (37.5° C.). The ion concentrations in the SBF are shown in Table 4. A cyclic potential spanning between −400 and +1600 mV was applied at a scanning rate of 600 mV/h. Before the electrochemical tests, the medium was purged with nitrogen for 1 h to remove dissolved oxygen and nitrogen purging continued throughout the measurements. The SBF taken from each sample after the corrosion test was analyzed for Ni and Ti employing inductively coupled plasma mass spectrometry (ICPMS) (Perkin Elmer, PE SCIEX ELAN6100, USA). The amounts of Ni leached from all treated samples were significantly reduced. The magnitudes were only about 0.03 to 0.04% of that of the control samples. The ion concentrations in the SBF are shown in Table 4.

TABLE 3

Amounts of Ni and Ti ions detected in SBF by ICPMS after electrochemical tests

| Sample | Ni content (ppm) Ni | Ti content (ppm) Ti |
|---|---|---|
| Control | 30.2324 | 0.1575 |
| C-treated | 0.0082 | 0.057 |
| N-treated | 0.0117 | 0.0527 |
| O-treated | 0.0123 | 0.002 |

TABLE 4

Ion concentration of SBF solution

| | Concentration (mM) | | | | | | | |
|---|---|---|---|---|---|---|---|---|
| | $Na^+$ | $K^+$ | $Ca^{2+}$ | $Mg^{2+}$ | $HCO_3^-$ | $Cl^-$ | $HPO_4^{2-}$ | $SO_4^{2-}$ |
| SBF | 142.0 | 5.0 | 2.5 | 1.5 | 4.2 | 148.5 | 1.0 | 0.5 |

Figure 2:
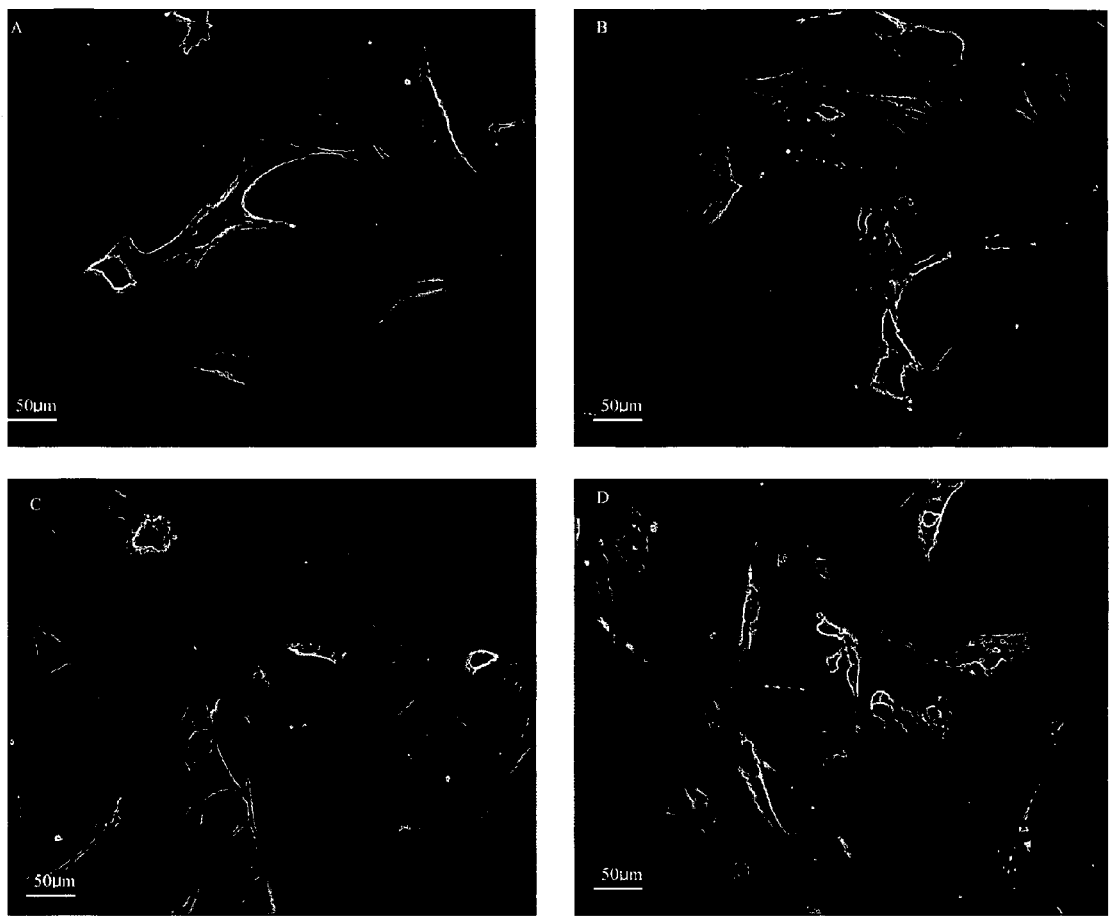
FIG. 2 includes photomicrographs of treated and untreated NiTi (control) after two days of cell culturing showing the EGFP expressing mouse osteoblasts. (A) NiTi alloy without surface treatment, (B) with nitrogen PIII implantation, (C) with acetylene PIII implantation, and (D) with oxygen PIII implantation.

FIG. 2 demonstrates that the nitrogen, acetylene and oxygen plasma-implanted samples are well tolerated by the EGFP-expressing osteoblasts. The osteoblasts were isolated from calvarial bones of 2-day-old mice that ubiquitously express an enhanced green fluorescent protein (EGFP) were used to culture in a Dulbecco's Modified Eagle Medium (DMEM) (Invitrogen) supplemented with 10% (v/v) fetal bovine serum (Biowest, France), antibiotics (100 U/ml of penicillin and 100 µg/ml of streptomycin), and 2 mM L-glutamine at 37° C. in an atmosphere of 5% $CO_2$ and 95% air. The specimens (1 mm thick and 5 mm in diameter) were fixed onto the bottom of a 24-well tissue culture plate (Falcon) using 1% (w/v) agarose. A cell suspension of 5,000 cells was seeded onto the surface of the untreated NiTi samples and the three types of plasma-implanted samples (oxygen, nitrogen, and acetylene). Cells were grown in one ml of medium and changed every two days. Cell attachment and proliferation were examined after the second day of culture. After culturing for two days, the cells started to attach to and proliferate on all the samples. Our results unequivocally demonstrate that there is no immediate cytotoxic effect on all of the surface treated samples.

It should be apparent to a person of ordinary skill that the improved alloys obtainable with the present invention can be used for a wide variety of applications, both as biomaterials and for other applications where such alloys might prove advantageous. For example, the alloys may be used to fashion orthopedic implants including replacement joints such as hips, knees, shoulders, elbows, fingers, or for rods, screws, nails, spinal implants and the like used for orthopedic purposes. They may also be used to form thin matches useful for making patches, tubing, and devices useful in urologic, cardiac, spinal, cerebrospinal, gastrointestinal, hepatobiliary, vascular, or esophageal surgery.

While the invention has been illustrated and described in detail in the drawings and foregoing description, the same is to be considered as illustrative and not restrictive in character, it is reasonable to think that only the preferred embodiments have been shown and described and that all changes and modifications that come within the spirit of the invention are desired to be protected.

REFERENCES CITED

The following references are incorporated by reference herein:

1. Berger-Gorbet, M., et al., "Biocompatibility Testing of NiTi Screws Using Immunohistochemistry on Sections Containing Metallic Implants," *Journal of Biomedical Materials Research*, 1996; 32(2):243-8.
2. Jia, W., et al., "Nickel Release from Orthodontic Arch Wires and Cellular Immune Response to Various Nickel Concentrations," *Journal of Biomedical Materials Research*, 1999; 48(4):488-95.
3. Es-Souni M., et al., "On the Properties of Two Binary NiTi Shape Memory Alloys: Effects of Surface Finish on the Corrosion Behavior and In Vitro Biocompatibility," *Biomaterials*, 2002; 23(14):2887-2894.
4. Shih, C-C., et al., "The Cytotoxicity of Corrosion Products of Nitinol Stent Wire on Cultured Smooth Muscle Cells," *Journal of Biomedical Materials Research*, 2000; 52(2):395-403.
5. Kapanen, A., et al., "Behavior of Nitinol in Osteoblast-like ROS-17 Cell Cultures," *Biomaterials*, 2002;23(3):645-650.
6. Kapanen, A., et al., "TGF-[beta]1 Secretion of ROS-17/2.8 Cultures on NiTi Implant Material," *Biomaterials*, 2002; 23(16):3341-3346.
7. Dalmau, L. B., et al., "A Study of Nickel Allergy," *Journal of Prosthet. Dent.* 1984; 52:116-119.
8. Lamster, I. B., et al., "Rapid Loss of Alveolar Bone Associated with Nonprecious Alloy Crowns in Two Patients with Nickel Hypersensitivity," *Journal of Periodont.* 1987; 58:486-492.
9. Espana, A., et al., "Chronic Urticaria After Implantation of 2 Nickel-Containing Dental Prostheses in a Nickel-Allergic Patient," *Contact Dermat.* 1989; 21:204-206.
10. Sanford, W. E. and Niboer, E., "Renal Toxicity of Nickel in Humans," Nriagu JO, ed. *Nickel and Human Health Current Perspectives*, Canada: John Wiley & Sons, Inc.; 1992. p 123-134.
11. Wu, S. K., et al., "A Study of Vacuum Carburization of an Equiatomic TiNi Shape Memory Alloy," *Scripta Materialia* 1997; 37:837-842.
12. Huber, P., et al., "Formation of TiN, TiC and TiCN by Metal Plasma Immersion Ion Implantation and Deposition," *Surface and Coatings Technology* 2003; 174-175: 1243-1247.
13. Liu, N., et al., "Effect of Nano-Micro TiN Addition on the Microstructure and Mechanical Properties of TiC Based Cermets," *Journal of the European Ceramic Society* 2002; 22:2409-2414.
14. Oliveira, M. M. and Bolton, J. D., "High-Speed Steels: Increasing Wear Resistance by Adding Ceramic Particles," *Journal of Materials Processing Technology* 1999; 92-93: 15-20.
15. Vaz, F., et al., "Structural, Optical and Mechanical Properties of Coloured $TiN_xO_y$ Thin Films," *Thin Solid Films* 2004; 447-448:449-454.
16. Kola, P. V., et al., "Magnetron Sputtering of Tin Protective Coatings for Medical Applications," *Journal of Materials Processing Technology* 1996; 56:422-430.
17. Tan, L. and Crone, W. C., "Surface Characterization of NiTi Modified by Plasma Source Ion Implantation," *Acta Materialia* 2002; 50:4449-4460.
18. Mändl, S., et al., "Investigation on Plasma Immersion Ion Implantation Treated Medical Implants," *Biomolecular Engineering* 2002; 19:129-132.
19. Nie, X., et al., "Deposition of Layered Bioceramic Hydroxyapatite/$TiO_2$ Coatings on Titanium Alloys Using a Hybrid Technique of Micro-Arc Oxidation and Electrophoresis," *Surface and Coatings Technology* 2000; 125: 407-414.
20. Lackner, J. M., et al., "Pulsed Laser Deposition of Titanium Oxide Coatings at Room Temperature—Structural, Mechanical and Tribological Properties," *Surface and Coatings Technology* 2004; 180-181:585-590.
21. Li, M. C., et al., "Corrosion Behavior of TiN Coated Type 316 Stainless Steel in Simulated PEMFC Environments," *Corrosion Science* 2004; 46:1369-1380.
22. Wan, G. J., Huang et al., "TiN and Ti—O/TiN Films Fabricated by PIII-D for Enhancement of Corrosion and Wear Resistance of Ti-6Al-4V," *Surface and Coatings Technology* 2004, In Press.
23. Pfohl, C., et al., "Evaluation of the Corrosion Behaviour of Wear-Resistant PACVD Coatings," *Surface and Coatings Technology* 1999; 112:114-117.
24. Maiya, P. S., et al., "Failure and Corrosion Resistance of TiN and TiC Coatings Deposited on Graphite by Chemical Vapor Deposition," *Surface and Coatings Technology* 1998; 102:218-222.
25. Leng, Y. X., et al., "Structure and Properties of Biomedical $TiO_2$ Films Synthesized by Dual Plasma Deposition," *Surface and Coatings Technology* 2002; 156:295-300.

We claim:

1. A method for altering the surface composition of a nickel titanium alloy part to increase biocompatibility, comprising exposing the surface of the nickel titanium alloy part to nitrogen, oxygen, or carbon by plasma immersion ion implantation, plasma immersion ion implantation and deposition, or ion beam immersion or implantation; whereby nitrogen, oxygen, or carbon ions bombard and penetrate the surface at a depth of at least about 50 nm, being implanted into the subsurface by acceleration under the influence of an electric field, and whereby the altered surface composition exhibits increased cell adhesion as compared to the unaltered surface composition.

2. The method according to claim 1, wherein the nickel titanium alloy is a shape memory alloy, and has a nickel content ranging from about 20-80% of nickel and 80-20% of titanium.

3. A method according to claim 1, wherein the surface implantation of elements enhances the surface mechanical properties of the alloy.

4. A method according to claim 3, wherein the enhanced surface mechanical properties include enhanced hydrophilicity, and enhanced corrosion and wear resistance.

5. A method according to claim 2, wherein the increased cell adhesion is increased adhesion of osteoblasts.

6. The method according to claim 5, whereby the altered surface composition has an atomic concentration of nickel that is less than 20% at a depth of 50 nm.

7. A method according to claim 2, wherein energy of the incident species used for surface treatment ranges from 500 eV to 100 keV for implantation and deposition, and 500 eV to 10 MeV for beam-line ion implantation.

8. A method according to claim 2, wherein the energy of the surface treatment of the nickel titanium alloy part ranges from 500 eVs to 1000 eVs for plasma immersion implantation, and 1000 eVs to 1000 MeVs for beam-line ion implantation.

9. A method according to claim 2, wherein direct current is applied with 0 Hz repetition and with infinite pulse duration to 5000 Hz.

10. A method in accordance with claim 9, wherein the nitrogen source is nitrogen gas.

11. A method in accordance with claim 9, wherein the carbon source is acetylene or a derivative thereof.

12. A method in accordance with claim 9, wherein the oxygen source is oxygen gas.

13. A method for altering the surface composition of a nickel titanium alloy part to increase biocompatibility, comprising exposing the surface of the nickel titanium alloy part to nitrogen, oxygen, or carbon by plasma immersion ion implantation, plasma immersion ion implantation and deposition, or ion beam immersion or implantation; whereby nitrogen, oxygen, or carbon ions bombard and penetrate the surface at a depth of at least about 50 nm, being implanted into the subsurface by acceleration under the influence of an electric field, and whereby the altered surface composition exhibits decreased cell apoptosis as compared to the unaltered surface composition.

14. The method according to claim 13, wherein the nickel titanium alloy is a shape memory alloy, and has a nickel content ranging from about 20-80% of nickel and 80-20% of titanium.

15. A method according to claim 13, wherein the surface implantation of elements enhances the surface mechanical properties of the alloy.

16. A method according to claim 15, wherein the enhanced surface mechanical properties include enhanced hydrophilicity, and enhanced corrosion and wear resistance.

17. A method according to claim 14, wherein the decreased cell apoptosis is decreased apoptosis of osteoblasts.

18. The method according to claim 17, whereby the altered surface composition has an atomic concentration of nickel that is less than 20% at a depth of 50 nm.

19. A method according to claim 13, wherein energy of the incident species used for surface treatment ranges from 500 eV to 100 keV for implantation and deposition, and 500 eV to 10 MeV for beam-line ion implantation.

20. A method according to claim 13, wherein the energy of the surface treatment of the nickel titanium alloy part ranges from 500 eVs to 1000 eVs for plasma immersion implantation, and 1000 eVs to 1000 MeVs for beam-line ion implantation.

21. A method according to claim 13, wherein direct current is applied with 0 Hz repetition and with infinite pulse duration to 5000 Hz.

22. A method in accordance with claim 21, wherein the nitrogen source is nitrogen gas.

23. A method in accordance with claim 21, wherein the carbon source is acetylene or a derivative thereof.

24. A method in accordance with claim 21, wherein the oxygen source is oxygen gas.

25. A method for altering the surface composition of a nickel titanium alloy part to yield the improved surface mechanical properties of increased hardness and improved corrosion resistance comprising exposing the surface of the nickel titanium alloy part to nitrogen, oxygen, or carbon by plasma immersion ion implantation, plasma immersion ion implantation and deposition, or ion beam immersion or implantation; whereby nitrogen, oxygen, or carbon ions bombard and penetrate the surface at a depth of at least about 50 nm, being implanted into the subsurface by acceleration under the influence of an electric field, and whereby the altered surface composition exhibits increased hardness and improved corrosion resistance as compared to the unaltered surface composition.

* * * * *